United States Patent [19]

Biel et al.

[11] 4,107,172
[45] Aug. 15, 1978

[54] URICOSURIC DIURETIC COMPOSITION

[75] Inventors: John Hans Biel, Lake Bluff, Ill.;
Dilbagh S. Bariana, Cote St. Luc;
Anthony K. L. Fung, Pierrefonds, both of Canada

[73] Assignee: Abbott Laboratories, North Chicago, Ill.

[21] Appl. No.: 447,182

[22] Filed: Mar. 1, 1974

[51] Int. Cl.² .................. C07D 257/04; A61K 31/41
[52] U.S. Cl. ..................... 260/308 D; 260/332.3 R; 424/269
[58] Field of Search ............... 260/308 D, 332.2 A

[56] References Cited
U.S. PATENT DOCUMENTS

| | | | |
|---|---|---|---|
| 3,531,493 | 9/1970 | Gittos et al. | 260/308 D |
| 3,706,768 | 12/1972 | Bays | 260/308 D |
| 3,758,506 | 9/1973 | Godfroid et al. | 260/332.2 A |

OTHER PUBLICATIONS

Juby et al., J. Med. Chem., vol. 12, pp. 396–401 (1969).
Juby et al., J. Med. Chem., vol. 11, pp. 111–117 (1968).
Buchanan et al., J. Med. Chem., vol. 12, pp. 1001–1006 (1969).

*Primary Examiner*—Alton D. Rollins
*Attorney, Agent, or Firm*—Robert L. Niblack; Vincent A. Mallare

[57] ABSTRACT

The present invention provides a therapeutically active composition having uricosuric, diuretic and antihypertension properties. The composition contains, as its active ingredient, a tetrazole compound having the structural formula:

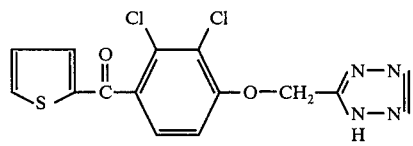

1 Claim, No Drawings

URICOSURIC DIURETIC COMPOSITION

STATEMENT OF THE INVENTION

The present invention is mainly directed to (1) all types of hypertension, (2) edema of all types (e.g., congestive heart failure, pulmonary edema, nephrosis, ascites, premenstrual tension, pregnancy, etc.), (3) hyperuricemia due to any cause, and (4) as an adjuvant to therapy to drugs which are lost due to rapid renal excretion. It may also be used to promote the excretion of toxic drugs and chemicals. This combination of effects represents a valuable new tool in the treatment of hypertension, edema and hyperuricemia.

It is thus an object of the present invention to provide a composition for treatment of hypertension in warm-blooded animals; it is another object of this invention to provide a composition for the treatment of hyperuricemia; it is a further object of this invention to provide a composition for treatment of various forms of edema, including congestive heart failure. In conjunction with these objects, it is an object of this invention to provide a diuretic composition in dosage unit form that virtually avoids all dangers of overdosing or toxic side effects.

These and other objects are accomplished by providing a medicinal composition consisting essentially of a tetrazole compound of the formula:

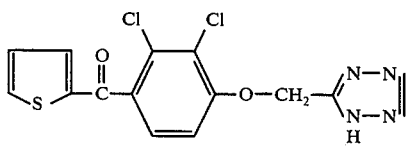

The above compound has particular activity as a uricosuric-diuretic and antihypertensive agent. In contrast to the presently available antihypertensive diuretics, this compound will produce potential diuretic and antihypertensive effects without the retention of uric acid. In fact, the composition actually promotes the excretion of uric acid which makes it superior to all other available drugs or compounds in this therapeutic category. This drug compound may be used alone for the treatment of hypertension and edema due to any cause or it may be used in conjunction with other diuretics and antihypertensives, and antihypertensives which have a propensity or activity for the retention of uric acid. The surprising characteristic of the present compound is that it will reduce the blood pressure as well as increase the excretion of uric acid in an amount of between 50 and 600% over the normal uric acid excretion of warm-blooded animals.

The present compound may be administered to warm-blooded animals orally or parenterally. It will be generally administered with a pharmaceutical carrier. The term "pharmaceutical carrier," for the purpose of the present invention, is intended to refer to any medium that is suitable for the preparation of a dosage unit form, and thus includes the tablet medium, a pharmaceutically acceptable vehicle or solvent such as is ordinarily used in the preparation of intravenous or intramuscular solutions.

A pharmaceutical composition containing the compound can be administered without danger to warm-blooded animals in parenteral or oral dosage form. For oral administration, amounts of from 0.01 to 200 mg./kg. per day per patient are extremely useful, with the total dose of about 3 gms. per day being a suitable range for large animals, including humans. The whole dosage range described increases the total urinary uric acid excretion from about 1.5 to about 6.5 fold in most animals. From these figures, it is apparent that the new uricosuric diuretic composition is particularly effective in increasing the excretion of uric acid in most animals.

For all dosage forms, the above exemplified tetrazole compound can be placed in capsules, formulated into pills, wafers or tablets in the usual fashion together with pharmaceutical carriers well known in the art. Tablets may be prepared for immediate release of the active compound or they may be made enteric, i.e., whereby the active ingredient is released slowly over a period of several hours from within the intestinal tract.

In order to illustrate the manner in which the above tetrazole compound may be prepared and the properties of the compound, reference is made to the following examples, which, however, are not meant to limit or restrict the scope of the invention in any respect.

EXAMPLE I

Preparation of 4-(2-thienylketo)-2,3-Dichloroanisole 9.1 g. (0.07 mole) of aluminum chloride was added to a mixture of 11 g. (0.075 mole) of thiophene-2-carboxylic acid chloride and 10 g. (0.056 mole) of 2,3-dichloroanisole in 40 ml. of methylene chloride. The solution was warmed to 45° C. for 45 minutes and poured onto ice. Then, 50 ml. of concentrated hydrochloric acid was added and the solid product filtered. After crystallization from 1,2-dichloroethane, 12 g. (75%) of 4-(2-thienylketo)-2,3-dichloroanisole, m.p. 112–114, was obtained.

EXAMPLE 2

Preparation of 4-(2-thienylketo)-2,3-Dichlorophenol 14 g. (0.049 mole) of 4-(2-thienylketo)-2,3-dichloroanisole was dissolved in 100 ml. of dry benzene. 21 g. (0.16 mole) of aluminum chloride was added and the mixture was refluxed for 2 hours. After being poured into cold water, the product was filtered and dissolved in 10% sodium hydroxide. The clear solution was acidified with 10% hydrochloric acid and the product collected by filtration and recrystallized from 1,2-dichloroethane to yield 8 g. (60%) of 4-(2-thienylketo)-2,3-dichlorophenol, m.p. 141–142.

EXAMPLE 3

Preparation of 4-(2-thienylketo)-2,3-Dichlorophenoxyacetonitrile

The reaction for preparing 4-(2-thienylketo)-2,3-dichlorophenoxyacetonitrile (II) is represented by the structural formulas:

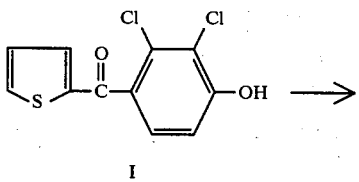

I

-continued

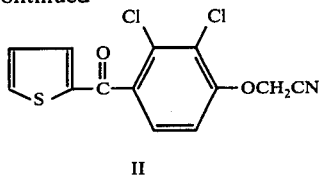

II

In this preparation, a mixture of 2.73 g. (0.01 mole) of 4-(2-thienylketo)-2,3-dichlorophenol (I), 0.75 g. (0.01 mole) of chloroacetonitrile, 0.96 g. (0.014 mole) of potassium carbonate and 0.01 g. of potassium iodide in 10 ml. of methylethylketone was refluxed for 1½ hours. The reaction mixture was filtered hot and the solvent was evaporated under vacuum. The residue was crystallized from acetone-water to yield 2 g. (70%) of 4-(2-thienylketo)-2,3-dichlorophenoxyacetonitrile (II), m.p. 125°–126°.

Analysis calculated for: $C_{13}H_7Cl_2NO_2S$: Theory: C, 50.00; H, 2.24; N, 4.49; Found: C, 49.85; H, 2.20; N, 4.52

EXAMPLE 4

Preparation of 5-[4-(2-thienylketo)-2,3-Dichlorophenoxymethyl]Tetrazole

The reaction for preparing the 5-[4-(2-thienylketo)-2,3-dichlorophenoxymethyl]tetrazole (III) is illustrated by the structural formulas:

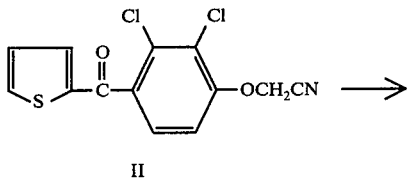

II

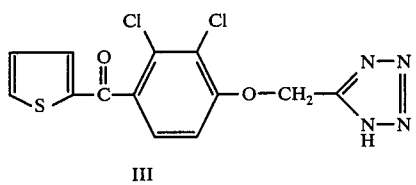

III

In this preparation, a mixture of 1.56 g. (0.005 mole) of 4-(2-thienylketo)-2,3-dichlorophenoxyacetonitrile (II), 0.39 g. (0.006 mole) of sodium azide and 0.70 g. of aluminum chloride in 30 ml. of tetrahydrofurane was refluxed for 24 hours. The reaction mixture was cooled and neutralized with dilute HCl. The solid precipitate was filtered and crystallized from ethylacetate to give 1.2 g. (70%) of 5[4-(2-thienylketo)-2,3-dichlorophenoxymethyl]tetrazole (III), m.p. 202°–204°.

Analysis calculated for: $C_{13}H_8Cl_2N_4O_2S$: Theory: C, 43.95; H, 2.26; N, 15.80; Found: C, 43.76; H, 2.26; N, 15.72

EXAMPLE 5

Uricosuric Activity in Anesthetized Cebus Monkeys (Cebus Capucinus)

Female Cebus capucinus monkeys weighing 1.3–1.8 kg. were immobilized with phencyclidine hydrochloride, 1 mg./kg., intramuscularly and anesthetized with sodium pentabarbital, 15 mg./kg., intravenously. The trachea was incised just caudal to the larynx and was cannulated to provide a clear airway. Both femoral arteries were cannulated to record arterial blood pressure and to collect blood samples. A femoral vein was cannulated for infusion of solution. The urinary bladder was catheterized through the urethral opening for collection of urine samples. Lead II electrocardiogram was recorded to monitor the heart rate.

On completion of surgical preparation of the monkey, a priming dose of inulin, 50 mg./kg. (20 mg./ml. solution) was administered intravenously. It was followed by an infusion of inulin at the rate of 4 mg./min. The infusion rate was adjusted to deliver 0.38 ml./min. The infusion solution also included, in addition to inulin, uric acid in a concentration suitable to deliver 0.6 mg./kg./min., 0.15% lithium carbonate, and 5% mannitol. The present tetrazole drug was dissolved or suspended in the same solution that contained the priming dose of inulin (that is, a single dose of the tetrazole drug was injected at the beginning of the experiment).

The bladder was emptied and the urine was discarded at the time of priming with inulin. Urine samples were collected every 30 minutes thereafter. The last sample was collected at 270 minutes. The volume of each urine sample was measured and was recorded. Two ml. blood samples were collected at the midpoint of the interval between collection of two urine samples.

The blood samples were centrifuged to obtain the plasma. Analysis of the plasma and urine was done to determine osmolality and the concentration of sodium, potassium, chloride, inulin and uric acid.

The diuretic and uricosuric activities of the tetrazole drug at 30 mg./kg., intravenously, were measured in four cebus monkeys. The results of each experiment on uric acid and urine excretion are tabulated in Table 1. The cumulative activities were compared to those in a group of 11 cebus monkeys receiving no drug, and are summarized in Table 2.

Statistical analysis of the data indicates that significant increases in uric acid and urine excretion were present at all collection periods. When compared to control monkeys up through the 2 hour collection period, the present tetrazole drug exhibited 10 fold increases in uric acid excretion and 2 fold increases in urine excretion. At the 270 minute collection period, 6 fold increases in uric acid excretion and 1.5 fold increases in urine excretion were still present. When the standard positive control uricosuric agent, probenecid, was tested at 25 mg./kg. intravenously in another group of monkeys, 2.5 fold increases in uric acid excretion were evident at the 2 hour collection period. No significant increases in uric acid excretion were present at the 270 minute collection period. Probenecid is sold under the tradename BENEMID, by Merck, Sharp & Dohme of West Point, Pa.

From the results recorded in the tables, it is clear that the tetrazole drug exhibited uricosuric and diuretic activities in the cebus monkey when administered intravenously at 30 mg./kg. These activities were substantial and of long duration. On a mg. for mg. basis, the tetrazole drug appears to be at least 3 times as active as probenecid in increasing uric acid excretion.

TABLE 1

EFFECT OF INTRAVENOUS TETRAZOLE DRUG, 30 MPK, ON URIC ACID EXCRETION IN CEBUS MONKEYS
TOTAL URIC ACID EXCRETED (MG/KG)

| Monkey Weight (Kg.) | Minutes After Administration of Tetrazole Drug | | | | | | | | |
|---|---|---|---|---|---|---|---|---|---|
| | 30 | 60 | 90 | 120 | 150 | 180 | 210 | 240 | 270 |
| 1.85 | 3.850 | 8.905 | 12.685 | 14.791 | 15.641 | 16.127 | 16.559 | 16.996 | 17.601 |
| 1.70 | 3.394 | 9.274 | 15.389 | 22.477 | 26.948 | 31.183 | 35.763 | 39.428 | 42.501 |
| 1.35 | 6.238 | 16.914 | 24.425 | 32.241 | 40.490 | 47.757 | 53.370 | 58.409 | 60.940 |
| 1.60 | 7.422 | 15.215 | 24.605 | 30.466 | 33.666 | 36.762 | 39.632 | 43.042 | 46.090 |
| Mean | 5.226 | 12.577 | 19.276 | 24.994 | 29.186 | 32.957 | 36.331 | 39.469 | 41.783 |
| ±S.E.M. | 0.962 | 2.045 | 3.075 | 4.009 | 5.294 | 6.582 | 7.596 | 8.547 | 8.995 |

S.E.M. is Standard Error of Mean

TABLE 2

COMPARATIVE EFFECTS OF INTRAVENOUS TETRAZOLE DRUG AND PROBENECID TO CONTROL EXPERIMENTS ON URIC ACID EXCRETION IN CEBUS MONKEYS
TOTAL URIC ACID EXCRETED (MG/KG) MEAN ± S.E.M.

| Drug | Dose mg/kg i.v. | No. of Monkeys | Minutes After Administration of Tetrazole Drug | | | | | | |
|---|---|---|---|---|---|---|---|---|---|
| | | | 30 | 90 | 120 | 180 | 210 | 240 | 270 |
| None | 0 | 11 | 0.5±0.05 | 2.5±0.25 | 3.7±0.38 | 6.4±0.70 | 7.9±0.87 | 9.3±1.10 | 10.7±1.34 |
| Tetrazole | 30 | 4 | 5.2±0.96 $P<0.001$ | 19.3±3.08 $P<0.001$ | 25.0±4.01 $P<0.001$ | 33.0±6.58 $P<0.001$ | 36.3±7.60 $P<0.001$ | 39.5±8.55 $P<0.001$ | 41.8±9.00 $P<0.001$ |
| Probenecid | 25 | 6 | 2.1±0.29 $P<0.001$ | 7.1±0.84 $P<0.001$ | 9.1±1.10 $P<0.001$ | 12.4±1.81 $P<0.005$ | 13.8±2.17 $P<0.01$ | 15.0±2.47 $P<0.05$ | 16.0±2.69 NS |

S.E.M. is Standard Error of Mean.
P is the significance level of a 2 sample t-test.
NS means not significant.

EXAMPLE 6

Diuretic Activity in Anesthetized Dog

A female beagle dog weighing 11.3 kg. was deprived of food and water 12–18 hours prior to the experiment. The dog was anesthetized with 3 mg./kg. of morphine sulfate, subcutaneously, followed 30 minutes later by 250 mg./kg. of barbital sodium, intravenously. The trachea was intubated to provide a clear airway. A femoral artery was cannulated to record arterial blood pressure and to collect blood samples. A femoral vein was cannulated for infusion of solutions. Both ureters were cannulated for collection of total urinary outflow.

On completion of surgical preparation of the dog, a continuous infusion of 0.9% saline at the rate of 0.6 ml./kg./min. was started and continued for 30 minutes. A priming dose of 35 mg. of inulin per 1.5 ml. of isotonic saline per kg. was then administered intravenously, followed by a maintenance dose of 1.1 mg./0.3 ml. isotonic saline/kg./minute. During an equilibration period of one hour, urine samples were collected at 10 minute intervals and the volume of each sample was measured and recorded. At the end of one hour (or longer if equilibrium was not achieved) three consecutive "control" urine and blood samples were collected. Each blood sample consisted of 4–5 ml. of arterial blood drawn at midpoint of the interval between the collection of two urine samples. Following the collection of the last control sample of urine, the experimental drug was injected intravenously. The infusion of inulin and collection of urine and blood samples was continued as before.

The blood samples were centrifuged to obtain the plasma. Analysis of plasma and urine was done to determine the concentrations of sodium, potassium, chloride and inulin. Plasma and urine osmolality was measured by standard procedures.

A 50 mg./kg. dose of the present tetrazole drug was administered intravenously to an 11.3 kg. dog. The calculated dose was administered as a 5% suspension in 25% propylene glycol. The peak effect on urine volume, urinary concentrations of sodium, potassium and chloride, and on systemic arterial blood pressure are presented in Table 3.

The tetrazole drug caused an increase in urinary volume, sodium, potassium, and chloride. These results indicate that the tetrazole drug has a significant diuretic and saluretic potency.

The tetrazole drug exhibited diuretic and saluretic properties at a dose of 50 mg./kg. intravenously.

TABLE 3

EFFECT OF TETRAZOLE DRUG ON URINE VOLUME AND ELECTROLYTE CONCENTRATION IN DOG

| Dog | | Dose | Blood Pressure (mm Hg) | | Urine Volume (ml/min) | | | | Sodium Excretion (μEq/kg/min) | |
|---|---|---|---|---|---|---|---|---|---|---|
| Wt (kg) | Sex | (mg/kg) | Control | After | Control | After | Peak | Dur. | Control | After |
| 11.3 | F | 50 | 106/70 | 100/72 | 0.15 | 2.30 | 40' | 80' | 3.74 | 39.69 |

| Dog | | Dose | Potassium Excretion (μEq/kg/min) | | Chloride Excretion (μEq/kg/min) | |
|---|---|---|---|---|---|---|
| Wt (kg) | Sex | (mg/kg) | Control | After | Control | After |
| 11.3 | F | 50 | 1.04 | 4.47 | 1.16 | 36.02 |

EXAMPLE 7

Antihypertensive Activity in Spontaneously Hypertensive (SH) Rats

Adult male SH rats of the Okamoto strain are trained to be restrained in a wire mesh cylinder for measurement of blood pressure by an indirect procedure developed at Abbott Laboratories. Half an hour prior to blood pressure measurement, the rats are placed in a warm chamber maintained at a constant temperature of 31° C. An occluding cuff, attached to a programmed sphygmonanometer, is placed near the base of the tail of each rat and the pressure in the cuff is increased automatically from zero to 250 mm Hg at a rate of 10 mm Hg per second. The cuff is then deflated at the same rate. The total time required for each cycle of inflation and deflation of the cuff is 50 seconds and the interval between successive cycles is 1 minute. A photocell is placed distal to the cuff to pick up the arterial pulse wave. As pressure in the cuff increases, the pulse wave completely disappears at a point where cuff pressure just exceeds the systolic arterial blood pressure. During deflation, the pulse wave reappears at approximately the same pressure. Five interference free signals obtained during deflation are recorded for each rat. Only those rats with a systolic blood pressure of 180 mm Hg or more during the control period are used in this study. A model 7 Grass Polygraph is used to record the cuff pressure and the arterial pulse wave.

Doses of 100 and 300 mg./kg. of the present tetrazole drug were administered orally to four SH rats each. A dose of 1000 mg./kg. was given orally to two SH rats.

The data presented in Table 4 indicates that the tetrazole drug exhibits an antihypertensive activity in SH rats. This activity appears to be of a long (more than 24 hours) duration.

Table 4
EFFECTS OF ORAL ADMINISTRATION OF TETRAZOLE DRUG ON SYSTOLIC ARTERIAL BLOOD PRESSURE IN SPONTANEOUSLY HYPERTENSIVE (SH) RATS

| Dose of the Tetrazole Drug (mg/kg) | 100 | | | | | 300 | | | | | 1000 | | |
|---|---|---|---|---|---|---|---|---|---|---|---|---|---|
| Rat No. | 1 | 2 | 3 | 4 | Mean ±S.E.M. | 5 | 6 | 7 | 8 | Mean ±S.E.M. | 9 | 10 | Mean ±S.E.M. |
| Control systolic blood pressure (mm Hg) | 246 | 203 | 207 | 211 | 216.8 ±9.9 | 209 | 205 | 247 | 208 | 217.3 ±10.0 | 200 | 213 | 206.5 ±6.5 |
| Systolic blood pressure 24 hours after tetrazole drug administration (mm Hg) | 204 | 202 | 186 | 162 | 188.5 ±9.7 | 176 | 168 | 198 | 184 | 181.5 ±6.4 | 120 | 128 | 124.0 ±4.0 |
| Percent change | −17 | 0 | −10 | −23 | −12.5 ±4.9 | −16 | −18 | −20 | −12 | −16.5 ±1.7 | −40 | −40 | −40.0 ±0.0 |

S.E.M. is Standard Error of Mean

We claim:
1. A tetrazole compound of the formula

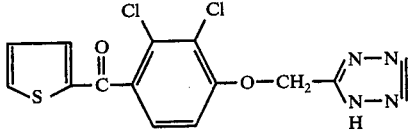

* * * * *